United States Patent
Hinokitani et al.

(10) Patent No.: US 11,413,224 B2
(45) Date of Patent: Aug. 16, 2022

(54) EXTERNAL PREPARATION FOR SKIN FOR WRINKLE IMPROVEMENT

(71) Applicant: Pola Chemical Industries, Inc., Fukuroi (JP)

(72) Inventors: Toshihiro Hinokitani, Yokohama (JP); Shigetsugu Homma, Yokohama (JP)

(73) Assignee: Pola Chemical Industries, Inc., Shizuoka (JP)

( * ) Notice: Subject to any disclaimer, the term of this patent is extended or adjusted under 35 U.S.C. 154(b) by 802 days.

(21) Appl. No.: 16/306,881

(22) PCT Filed: Jun. 21, 2017

(86) PCT No.: PCT/JP2017/022824
§ 371 (c)(1),
(2) Date: Dec. 3, 2018

(87) PCT Pub. No.: WO2017/221973
PCT Pub. Date: Dec. 28, 2017

(65) Prior Publication Data
US 2021/0030631 A1    Feb. 4, 2021

(30) Foreign Application Priority Data
Jun. 24, 2016  (JP) .............................. JP2016-125685

(51) Int. Cl.
| A61K 8/02  | (2006.01) |
| A61K 8/04  | (2006.01) |
| A61K 8/64  | (2006.01) |
| A61K 8/81  | (2006.01) |
| A61K 8/891 | (2006.01) |
| A61Q 19/08 | (2006.01) |

(52) U.S. Cl.
CPC .............. *A61K 8/025* (2013.01); *A61K 8/042* (2013.01); *A61K 8/64* (2013.01); *A61K 8/8152* (2013.01); *A61K 8/891* (2013.01); *A61Q 19/08* (2013.01)

(58) Field of Classification Search
CPC .......... A61K 8/02; A61K 8/025; A61K 8/042; A61K 8/64; A61K 8/8152; A61K 8/891; A61P 17/00; A61Q 19/08
USPC ....................................................... 424/401
See application file for complete search history.

(56) References Cited

U.S. PATENT DOCUMENTS

| 5,296,591 A    | 3/1994  | Hemmi et al.  |            |
| 6,235,292 B1   | 5/2001  | Bara et al.   |            |
| 6,610,748 B1 * | 8/2003  | Yabuta ...... | A61K 38/04 |
|                |         |               | 514/621    |
| 2003/0087831 A1| 5/2003  | Ohmoto et al. |            |
| 2003/0203853 A1| 10/2003 | Yabuta et al. |            |
| 2003/0207432 A1| 11/2003 | Takakura et al.|           |
| 2007/0110778 A1| 5/2007  | Anderson      |            |

FOREIGN PATENT DOCUMENTS

| EP | 0494071    A2 | 7/1992  |
| EP | 1136064    A2 | 9/2001  |
| JP | H04-297446 A  | 10/1992 |
| JP | 2001-294510 A | 10/2001 |
| JP | 3242874    B  | 12/2001 |
| JP | 2002-255847 A | 9/2002  |
| JP | 2003-300851 A | 10/2003 |
| JP | 3492483    B  | 2/2004  |
| JP | 2004-123637 A | 4/2004  |
| JP | 2005-041795 A | 2/2005  |
| JP | 4320791    B2 | 8/2009  |
| RU | 2073684    C1 | 2/1997  |

(Continued)

OTHER PUBLICATIONS

Omura Takayuki,TW201242616A, bib , machine translattion.*
Omura Takayuki,TW201242616,Description , machine translattion.*
Omura Takayuki,TW201242616,claims , machine translattion.*
Sutyagin, V.M., et al., "Chemistry and Physics of Polymers Study guide" Tomsk Polytechnic University, 2003, p. 132,140,142,151,173.
Kharkevich D.A., GEOTAR-Media, Farmakologiya (Pharmacology: A Handbook), 10th Ed., 2010, p. 73.
Office Action and Search Report issued in corresponding Russian Patent Application No. 2018142778 dated Oct. 13, 2020.
International Search Report received in International Patent Application No. PCT/JP2017/022824 dated Sep. 19, 2017.

(Continued)

*Primary Examiner* — Ali Soroush
*Assistant Examiner* — Courtney A Brown
(74) *Attorney, Agent, or Firm* — Knobbe, Martens, Olson & Bear, LLP

(57) ABSTRACT

An oil-gel-form external preparation for skin contains a compound represented by the following General Formula (1), an isomer thereof, and/or a pharmaceutically acceptable salt thereof. A partially cross-linked methyl polysiloxane; allows easy penetration of the compound from the preparation into the skin while enhancing the percutaneous absorbability and improving the intradermal retentivity.

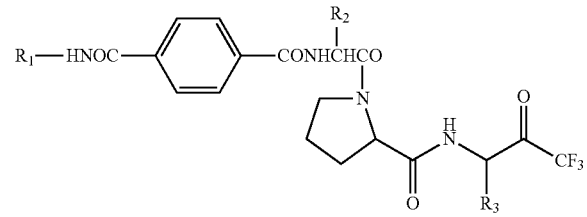

(1)

In the formula, $R_1$ represents a $C_1$-$C_4$ linear or branched alkyl group substituted by a carboxyl group(s), or a $C_1$-$C_4$ linear or branched alkyl group substituted by a carboxylic acid ester group(s) having a $C_1$-$C_4$ alkyl chain, and $R_2$ and $R_3$ each independently represent a $C_1$-$C_4$ linear or branched alkyl group.

7 Claims, No Drawings

(56) References Cited

FOREIGN PATENT DOCUMENTS

| TW | 201242616 A | * | 11/2012 |
|----|----|----|----|
| WO | WO 98/27998 A1 | | 7/1998 |
| WO | WO 99/43352 A1 | | 9/1999 |
| WO | WO 01/26685 A1 | | 4/2001 |
| WO | WO 01/40263 A1 | | 6/2001 |
| WO | WO 2012/124436 A1 | | 9/2012 |

OTHER PUBLICATIONS

Notification of Transmittal of Copies of Translation of the International Preliminary Report on Patentability issued in PCT/JP2017/022824 dated Jan. 3, 2019.
Suzuki, et al., CMC Technical Library 268, Development Technology of Anti-Aging, Whitening, Moisturizing Cosmetics, CNC Publishing Co., Ltd., Jun. 30, 2001, pp. 157-161.
Shinguh et al., "Biochemical and pharmacological characterization of FK706, a novel elastase inhibitor", European Journal of Pharmacology, vol. 337, Aug. 19, 1997, pp. 63-71.
Extended Search Report issued in the corresponding EP Patent Application No. 17815441.5, dated Dec. 3, 2019.

* cited by examiner

EXTERNAL PREPARATION FOR SKIN FOR WRINKLE IMPROVEMENT

TECHNICAL FIELD

The present invention relates to an external preparation for skin suitable as a cosmetic (including a quasi-drug), more specifically, to an oil-gel-form external preparation for skin containing: 1) a compound represented by the following General Formula (1), an isomer thereof, and/or a pharmaceutically acceptable salt thereof; and 2) a partially cross-linked methyl polysiloxane.

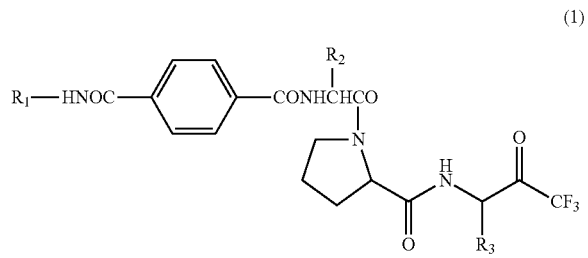

(1)

[In the formula, $R_1$ represents a $C_1$-$C_4$ linear or branched alkyl group substituted by a carboxyl group(s), or a $C_1$-$C_4$ linear or branched alkyl group substituted by a carboxylic acid ester group(s) having a $C_1$-$C_4$ alkyl chain, and $R_2$ and $R_3$ each independently represent a $C_1$-$C_4$ linear or branched alkyl group.]

BACKGROUND ART

A representative symptom of the skin aging phenomenon due to aging is wrinkle formation. Wrinkles can be roughly divided into shallow wrinkles formed on the skin surface, which can be improved by moisturization, and deep wrinkles formed by exposure to ultraviolet or accumulation of physical stimulation. Prevention or improvement of formation of the latter, deep wrinkles, is very difficult. A variety of wrinkle-improving agents have been developed to date (see, for example, Non-patent Document 1). Among such wrinkle-improving agents, those containing retinoic acid as an effective component are well known. Although retinoic acid has been approved as a therapeutic drug for wrinkles and acne in the United States, it has not been approved in Japan due to safety problems such as cutaneous stimulation. As other wrinkle-improving agents, a collagen production-promoting agent (see, for example, Patent Document 1), a hyaluronic acid production-promoting agent (see, for example, Patent Document 2), and the like have been reported. However, the above wrinkle-improving agents cannot be said to be sufficiently effective, and establishment of effective means has not yet been achieved. Possible causes of such a problem include the stability of the wrinkle-improving agents and external preparations for skin, and the presence of wrinkle-improving agents having a problem in, for example, the dermal permeability or retentivity.

An elastase inhibitor is a wrinkle-improving agent having an action mechanism different from those of the above wrinkle-improving agents. Elastin, one of the structural proteins present in the skin tissue, maintains the elasticity of the tissue by construction of a cross-linked structure. It is known that cutaneous stimulations such as exposure to ultraviolet cause overexpression and activation of the elastin-degrading enzyme elastase, thereby denaturing and destroying elastin to cause deterioration of the firmness and the elasticity of the skin, resulting in promotion of wrinkle formation. An elastase inhibitor inhibits the elastin-degrading enzyme to produce a preventive or improvement effect on wrinkle formation. On the other hand, although structural analysis and structure-activity relationship studies have been carried out for elastin-degrading enzymes and their substrates, it is difficult to realize a high enzyme inhibitory activity and selectivity by an organic low molecular substance. There are a number of peptides and their derivatives as components having a high enzyme inhibitory action (see, for example, Patent Document 3). Among such peptide-derivative elastase inhibitors, peptide derivatives such as WS7622A mono- or di-sulfuric acid esters are known (see, for example, Patent Document 4), and their practical application to ischemic diseases based on such a pharmacological action has been attempted. Compounds represented by the General Formula (1) are known to have a leukocyte elastase inhibitory action similarly to WS7622A, and reported to have an action to prevent or treat skin aging (see, for example, Patent Document 5). However, there is a concern that delivery of effective amounts of the peptides and their derivatives to wrinkle formation sites may be impossible since they have relatively large molecular sizes, and have chemical structural properties that are undesirable for delivery to the dermis, such as the presence of a plurality of amide bonds. In practice, transdermal administration of a peptide or its derivative often has a problem in terms of the stability of the effective component or the external preparation for skin, or in terms of the dermal permeability or retentivity, so that an expected effect cannot be obtained in many cases.

In general, in cases where a wrinkle-improving agent is to be included in an external preparation for skin such as a cosmetic, an aqueous formulation such as a lotion formulation, essence formulation, or cream formulation is selected. The elastase inhibitor, especially a peptide or its derivative expected to have a high elastase inhibitory activity, has a relatively high molecular weight, and has a chemical structure containing a small hydrophilic portion in a lipophilic portion. Therefore, in cases where an aqueous formulation is selected, and a wrinkle-improving agent is included therein, penetration of the wrinkle-improving agent from the skin surface into the dermis hardly occurs, and the agent tends to be detached in a short time due to sweat or the like. This results in a very low bioavailability, and the expected preventive or improvement action on wrinkle formation is often not produced. On the other hand, conventional oil gel preparations prepared by solidifying a liquid oil using a wax or the like have advantages such as suppression of the above-described detachment of a wrinkle-improving agent due to sweat or the like, and suppression of degradation of a wrinkle-improving agent which is instable to water. However, such preparations often show rather poor penetration or infiltration into the dermis. The oil gel preparations also have problems in usability such as stickiness. Thus, for improving usability of oil gel preparations as cosmetics, an oil-gel-form external preparation for skin containing a silicone oil has been reported (see, for example, Patent Document 6 and Patent Document 7). Further, cosmetics as oil gel formulations containing a silicone oil are known to be less likely to undergo changes in the fragrance properties with time (see, for example, Patent Document 8).

There are also known techniques in which a cross-linked silicone elastomer (partially cross-linked methyl polysiloxane) is included in a cosmetic composition in order to improve the appearance of the entire skin including fine wrinkles, wherein a smooth thin film is formed by application of the composition to the skin to flatten fine wrinkles and wrinkles, or in which spherical particles are further included to give a function as an optical diffuser that causes optical scattering on fine wrinkles and wrinkles to change the surface optometrics of the skin (see, for example, Patent Document 9).

PRIOR ART DOCUMENTS

Patent Documents

Patent Document 1: JP 2002-255847 A
Patent Document 2: JP 2004-123637 A
Patent Document 3: WO 2001/40263
Patent Document 4: WO 1998/27998
Patent Document 5: WO 1999/43352
Patent Document 6: JP 3242874 B
Patent Document 7: JP 3492483 B
Patent Document 8: JP 2003-300851 A
Patent Document 9: JP 2001-294510 A Non-Patent Document Non-patent Document 1: Development Technology of Anti-aging, Whitening, Moisturizing Cosmetics, CMC Publishing, supervised by Masato Suzuki, Chapter 2, Anti-aging Anti-wrinkle Functional Cosmetics

SUMMARY OF THE INVENTION

Problems to be Solved by the Invention

As described above, employment itself of an oil gel formulation as the formulation of a cosmetic is an already known technique. However, the influence of an oil-gel-form external preparation for skin containing an effective component intended for application to the skin, on transdermal absorption of the effective component has been unclear. Thus, no attempt has been made to include a compound represented by the General Formula (1) in such an oil gel preparation.

The present invention was carried out under such circumstances, and aims to provide a method for improving the dermal retentivity of a compound represented by the General Formula (1), an isomer thereof, and/or a pharmaceutically acceptable salt thereof.

Means for Solving the Problems

In view of such circumstances, the present inventors made an intensive effort in order to find a method for improving the dermal retentivity of a compound represented by the General Formula (1), an isomer thereof, and/or a pharmaceutically acceptable salt thereof. As a result, the present inventors discovered that, by including a compound represented by the General Formula (1), an isomer thereof, and/or a pharmaceutically acceptable salt thereof in an oil-gel-form external preparation for skin containing a cross-linked methyl polysiloxane as a structural base body, the balance between the ease of the presence of the compound in the external preparation for skin and the penetration into the skin can be improved, so that the dermal retentivity can be improved.

The present inventors also discovered that, by inclusion of a spherical powder in an oil-gel-form external preparation for skin, the external preparation for skin can have a decreased viscosity and an increased fluidity, leading to improved usability, better spreadability of the external preparation for skin on the skin, and improved transdermal absorption. Based on these findings, the present inventors discovered that an oil-gel-form external preparation for skin can improve the dermal retentivity of a compound represented by the General Formula (1) or the like in the external preparation for skin, thereby completing the present invention. More specifically, the present invention is as follows.

<1> An oil-gel-form external preparation for skin containing: 1) a compound represented by the following General Formula (1), an isomer thereof, and/or a pharmaceutically acceptable salt thereof; and 2) a partially cross-linked methyl polysiloxane.

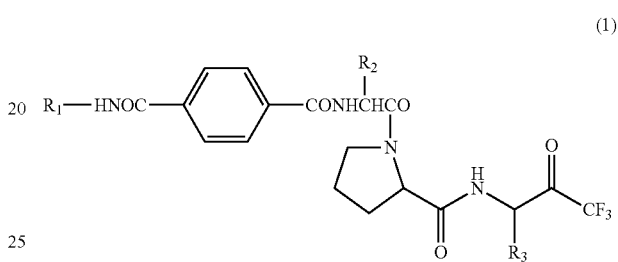

(1)

[In the formula, $R_1$ represents a $C_1$-$C_4$ linear or branched alkyl group substituted by a carboxyl group(s), or a $C_1$-$C_4$ linear or branched alkyl group substituted by a carboxylic acid ester group(s) having a $C_1$-$C_4$ alkyl chain, and $R_2$ and $R_3$ each independently represent a $C_1$-$C_4$ linear or branched alkyl group.]

<2> The oil-gel-form external preparation for skin according to <1>, wherein the compound represented by the General Formula (1) is a compound represented by the following General Formula (2), an isomer thereof, and/or a pharmaceutically acceptable salt thereof.

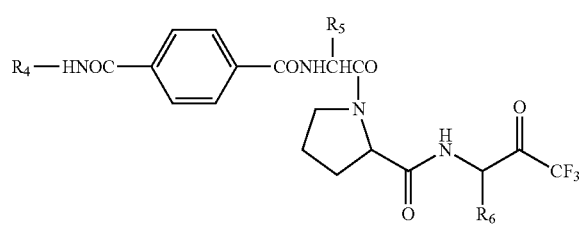

(2)

[In the formula, $R_4$ represents a $C_1$-$C_4$ linear or branched alkyl group substituted by a carboxyl group(s); and $R_5$ and $R_6$ each independently represent a $C_1$-$C_4$ linear or branched alkyl group.]

<3> The oil-gel-form external preparation for skin according to <2>, wherein the compound represented by the General Formula (2) is 3(RS)-[[4-(carboxymethylaminocarbonyl)phenylcarbonyl]-L-valyl-L-prolyl]amino-1,1,1-trifluoro-4-methyl-2-oxopentane represented by the following Formula (3), an isomer thereof, and/or a pharmaceutically acceptable salt thereof.

(3)

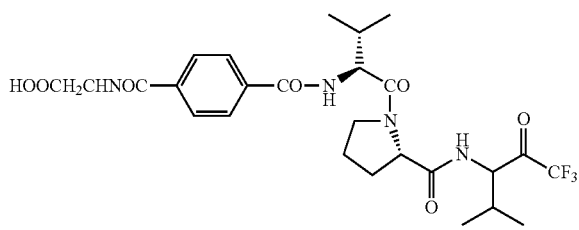

<4> The oil-gel-form external preparation for skin according to any one of <1> to <3>, further comprising a spherical powder.
<5> The oil-gel-form external preparation for skin according to <4>, wherein the spherical powder is an organic spherical powder.
<6> The oil-gel-form external preparation for skin according to <4> or <5>, wherein the spherical powder is polymethyl methacrylate.
<7> The oil-gel-form external preparation for skin according to any one of <4> to <6>, wherein the spherical powder is contained at 12 to 50% by mass with respect to the total amount of the external preparation for skin.

Effect of the Invention

By use of the oil-gel-form external preparation for skin of the present invention, a compound represented by the General Formula (1), an isomer thereof, and/or a pharmaceutically acceptable salt thereof can be delivered to the dermis, and the dermal retentivity of the compound can be improved, thereby providing solutions for cosmetic problems such as prevention or improvement of wrinkle formation.

DETAILED DESCRIPTION OF THE PREFERRED EMBODIMENT

<Compound Represented by General Formula (1), Isomer Thereof, and/or Pharmaceutically Acceptable Salt Thereof in Present Invention>

The oil-gel-form external preparation for skin of the present invention comprises: 1) a compound represented by the General Formula (1), an isomer thereof, and/or a pharmaceutically acceptable salt thereof; and 2) a partially cross-linked methyl polysiloxane. The oil-gel-form external preparation for skin of the present invention improves the dermal retentivity of the compound represented by the General Formula (1), the isomer thereof, and/or the pharmaceutically acceptable salt thereof, thereby producing an excellent preventive or improvement effect on wrinkle formation. The compound represented by the General Formula (1), the isomer thereof, and/or the pharmaceutically acceptable salt thereof in the present invention can be produced by, for example, a method described in JP 04-297446 A. Since the compound represented by the General Formula (1) in the present invention has an inhibitory activity on human leukocyte elastase, a therapeutic effect on cerebral ischemic diseases such as cerebral infarction can be expected. Further, as described in WO1999/43352, the compound has a preventive or therapeutic effect on skin aging. The compound represented by the General Formula (1) in the present invention has actions such as regeneration of elastic fibers in the papillary dermis, regeneration of fine collagen fibers in the dermal portion immediately beneath the epidermis, and an increase in the epidermal thickness, and produces a preventive or improvement effect on wrinkle formation based on such actions. Further, since the compound represented by the General Formula (1) in the present invention is an optically active compound having a plurality of asymmetric carbon atoms in its molecular structure, there are enantiomers and diastereomers as its isomers. Examples of the compound represented by the General Formula (1) in the present invention include racemic bodies, enantiomers, and diastereomers, and also compounds containing such isomers at arbitrary ratios.

Regarding the compound represented by the General Formula (1) in the present invention, in the formula, $R_1$ represents a $C_1$-$C_4$ linear or branched alkyl group substituted by a carboxyl group(s), or a $C_1$-$C_4$ linear or branched alkyl group substituted by a carboxylic acid ester group(s) having a $C_1$-$C_4$ alkyl chain, and $R_2$ and $R_3$ each independently represent a $C_1$-$C_4$ linear or branched alkyl group.

Preferred specific examples of the $R_1$ include carboxymethyl, carboxyethyl, carboxypropyl, carboxybutyl, methoxycarbonylmethyl, methoxycarbonylethyl, methoxycarbonylpropyl, methoxycarbonylbutyl, ethoxycarbonylmethyl, ethoxycarbonylethyl, ethoxycarbonylpropyl, ethoxycarbonylbutyl, propyloxycarbonylmethyl, propyloxycarbonylethyl, propyloxycarbonylpropyl, propyloxycarbonylbutyl, butyloxycarbonylmethyl, butyloxycarbonylethyl, butyloxycarbonylpropyl, and butyloxycarbonylbutyl. More preferred examples of the $R_1$ include carboxymethyl.

Preferred specific examples of each of the $R_2$ and the $R_3$ independently include methyl, ethyl, n-propyl, isopropyl, n-butyl, isobutyl, sec-butyl, and tert-butyl. More preferred examples of the $R_2$ and the $R_3$ include isopropyl.

Preferred examples of the compound represented by the General Formula (1), the isomer thereof, and/or the pharmaceutically acceptable salt thereof include compounds represented by the General Formula (2), isomers thereof, and/or pharmaceutically acceptable salts thereof. More preferred examples of the compound include 3-[[4-(carboxymethylaminocarbonyl)phenylcarbonyl]-valyl-prolyl]amino-1,1,1-trifluoro-4-methyl-2-oxopentane, isomers thereof, and/or pharmaceutically acceptable salts thereof. Still more preferred examples of the compound include 3(RS)-[[4-(carboxymethylaminocarbonyl)phenylcarbonyl]-L-valyl-L-prolyl]amino-1,1,1-trifluoro-4-methyl-2-oxopentane and sodium salt thereof (the sodium salt may be hereinafter referred to as KSK32).

The compound represented by the General Formula (1), the isomer thereof, and/or the pharmaceutically acceptable salt thereof in the present invention, when included in an oil-gel-form external preparation for skin together with a partially cross-linked methyl polysiloxane, enhance(s) the dermal retentivity, and improve(s) the preventive or improvement effect on wrinkle formation.

Regarding the compound represented by the General Formula (2) in the present invention, in the formula, $R_4$ represents a $C_1$-$C_4$ linear or branched alkyl group substituted by a carboxyl group(s); and $R_5$ and $R_6$ each independently represent a $C_1$-$C_4$ linear or branched alkyl group. The $R_4$ represents a $C_1$-$C_4$ linear or branched alkyl group substituted by a carboxyl group(s). Preferred specific examples of the $R_4$ include carboxymethyl, 1-carboxyethyl, 2-carboxyethyl, 1-carboxypropyl, 2-carboxypropyl, 3-carboxypropyl, 1-carboxybutyl, 2-carboxybutyl, 3-carboxybutyl, and 4-carboxybutyl. More preferred examples of the $R_4$ include carboxymethyl.

The $R_5$ and the $R_6$ each independently represent a $C_1$-$C_4$ linear or branched alkyl group. Preferred specific examples of the $R_5$ and the $R_6$ include methyl, ethyl, n-propyl, isopropyl, n-butyl, isobutyl, sec-butyl, and tert-butyl. More preferred specific examples of the $R_5$ and the $R_6$ include isopropyl. Regarding the compound represented by the General Formula (2), preferred specific examples of the compound include N-[4-[[(carboxymethyl)amino]carbonyl]benzoyl]-L-alanyl-N-[3,3,3-trifluoro-1-(1-methyl)-2-oxopropyl]-L-prolinamide, N-[4-[[(carboxyethyl)amino]carbonyl]benzoyl]-L-alanyl-N-[3,3,3-trifluoro-1-(1-methyl)-2-oxopropyl]-L-prolinamide, N-[4-[[(carboxypropyl)amino]carbonyl]benzoyl]-L-alanyl-N-[3,3,3-trifluoro-1-(1-methyl)-2-oxopropyl]-L-prolinamide, N-[4-[[(carboxybutyl)amino]carbonyl]benzoyl]-L-alanyl-N-[3,3,3-trifluoro-1-(1-methyl)-2-oxopropyl]-L-prolinamide, N-[4-[[(carboxymethyl)amino]carbonyl]benzoyl]-L-alanyl-N-[3,3,3-trifluoro-1-(1-ethyl)-2-oxopropyl]-L-prolinamide, N-[4-[[(carboxyethyl)amino]carbonyl]benzoyl]-L-alanyl-N-[3,3,3-trifluoro-1-(1-ethyl)-2-oxopropyl]-L-prolinamide, N-[4-[[(carboxypropyl)amino]carbonyl]benzoyl]-L-alanyl-N-[3,3,3-trifluoro-1-(1-ethyl)-2-oxopropyl]-L-prolinamide, N-[4-[[(carboxybutyl)amino]carbonyl]benzoyl]-L-alanyl-N-[3,3,3-trifluoro-1-(1-ethyl)-2-oxopropyl]-L-prolinamide, N-[4-[[(carboxymethyl)amino]carbonyl]benzoyl]-L-alanyl-N-[3,3,3-trifluoro-1-(1-methylethyl)-2-oxopropyl]-L-prolinamide, N-[4-[[(carboxyethyl)amino]carbonyl]benzoyl]-L-alanyl-N-[3,3,3-trifluoro-1-(1-methylethyl)-2-oxopropyl]-L-prolinamide, N-[4-[[(carboxypropyl)amino]carbonyl]benzoyl]-L-alanyl-N-[3,3,3-trifluoro-1-(1-methylethyl)-2-oxopropyl]-L-prolinamide, N-[4-[[(carboxybutyl)amino]carbonyl]benzoyl]-L-alanyl-N-[3,3,3-trifluoro-1-(1-methylethyl)-2-oxopropyl]-L-prolinamide, N-[4-[[(carboxymethyl)amino]carbonyl]benzoyl]-L-valyl-N-[3,3,3-trifluoro-1-(1-methyl)-2-oxopropyl]-L-prolinamide, N-[4-[[(carboxyethyl)amino]carbonyl]benzoyl]-L-valyl-N-[3,3,3-trifluoro-1-(1-methyl)-2-oxopropyl]-L-prolinamide, N-[4-[[(carboxypropyl)amino]carbonyl]benzoyl]-L-valyl-N-[3,3,3-trifluoro-1-(1-methyl)-2-oxopropyl]-L-prolinamide, N-[4-[[(carboxybutyl)amino]carbonyl]benzoyl]-L-valyl-N-[3,3,3-trifluoro-1-(1-methyl)-2-oxopropyl]-L-prolinamide, N-[4-[[(carboxymethyl)amino]carbonyl]benzoyl]-L-valyl-N-[3,3,3-trifluoro-1-(1-ethyl)-2-oxopropyl]-L-prolinamide, N-[4-[[(carboxyethyl)amino]carbonyl]benzoyl]-L-valyl-N-[3,3,3-trifluoro-1-(1-ethyl)-2-oxopropyl]-L-prolinamide, N-[4-[[(carboxypropyl)amino]carbonyl]benzoyl]-L-valyl-N-[3,3,3-trifluoro-1-(1-ethyl)-2-oxopropyl]-L-prolinamide, N-[4-[[(carboxybutyl)amino]carbonyl]benzoyl]-L-valyl-N-[3,3,3-trifluoro-1-(1-ethyl)-2-oxopropyl]-L-prolinamide, N-[4-[[(carboxymethyl)amino]carbonyl]benzoyl]-L-valyl-N-[3,3,3-trifluoro-1-(1-methylethyl)-2-oxopropyl]-L-prolinamide (3(RS)—N-[4-[[(carboxymethyl)amino]carbonyl]benzoyl]-L-valyl-N-[3,3,3-trifluoro-1-(1-methylethyl)-2-oxopropyl]-L-prolinamide), N-[4-[[(carboxyethyl)amino]carbonyl]benzoyl]-L-valyl-N-[3,3,3-trifluoro-1-(1-methylethyl)-2-oxopropyl]-L-prolinamide, N-[4-[[(carboxypropyl)amino]carbonyl]benzoyl]-L-valyl-N-[3,3,3-trifluoro-1-(1-methylethyl)-2-oxopropyl]-L-prolinamide, N-[4-[[(carboxybutyl)amino]carbonyl]benzoyl]-L-valyl-N-[3,3,3-trifluoro-1-(1-methylethyl)-2-oxopropyl]-L-prolinamide, isomers thereof, and/or pharmaceutically acceptable salts thereof. More preferred examples of the compound include N-[4-[[(carboxymethyl)amino]carbonyl]benzoyl]-L-valyl-N—[(RS)-3,3,3-trifluoro-1-(1-methylethyl)-2-oxopropyl]-L-prolinamide represented by General Formula (3), isomers thereof, and/or pharmaceutically acceptable salts thereof. As described above, the compound represented by General Formula (3) is also represented as 3(RS)-[[4-(carboxymethylaminocarbonyl)phenylcarbonyl]-L-valyl-L-prolyl]amino-1,1,1-trifluoro-4-methyl-2-oxopentane.

It should be noted that sodium salt of N-[4-[[(carboxymethyl)amino]carbonyl]benzoyl]-L-valyl-N—[(RS)-3,3,3-trifluoro-1-(1-methylethyl)-2-oxopropyl]-L-prolinamide may be hereinafter simply referred to as KSK32. It is the same compound as the above-described KSK32 although the designation is different.

The compound represented by the General Formula (1), the isomer thereof, and/or the pharmaceutically acceptable salt thereof in the present invention, when included in an oil-gel-form external preparation for skin together with a partially cross-linked methyl polysiloxane, enhance(s) the dermal retentivity, suppress(es) wrinkle formation, and shift(s) the balance between formation and disappearance of wrinkles toward the disappearance side, thereby improving the preventive or improvement effect on wrinkle formation.

The compound represented by the General Formula (1) in the present invention may be included as it is in the oil-gel-form external preparation for skin, or may be converted into the form of a salt by treatment with a pharmaceutically acceptable acid or base, to be used as a salt. Examples of the salt include inorganic acid salts such as hydrochloric acid salt, sulfuric acid salt, nitric acid salt, phosphoric acid salt, and carbonic acid salt; organic acid salts such as maleic acid salt, fumaric acid salt, oxalic acid salt, citric acid salt, lactic acid salt, tartaric acid salt, methanesulfonic acid salt, para-toluenesulfonic acid salt, and benzenesulfonic acid salt; alkali metal salts such as sodium salt and potassium salt; alkaline earth metal salts such as calcium salt and magnesium salt; organic amine salts such as triethylamine salt, triethanolamine salt, ammonium salt, monoethanolamine salt, and piperidine salt; and basic amino acid salts such as lysine salt and arginine acid salt. One or more of compounds represented by the General Formula (1), isomers thereof, and/or pharmaceutically acceptable salts thereof may be selected and included in the oil-gel-form external preparation for skin of the present invention.

For allowing production of the effects described above by the inclusion of the compound represented by the General Formula (1), the isomer thereof, and/or the pharmaceutically acceptable salt thereof of the present invention in the oil-gel-form external preparation for skin, these are preferably contained at 0.01% by mass to 10% by mass, more preferably contained at 0.1% by mass to 5% by mass with respect to the total amount of the external preparation for skin. This is because, in cases where the amount of the compound represented by the General Formula (1), the isomer thereof, and/or the pharmaceutically acceptable salt thereof contained in the oil-gel-form external preparation for skin is too small, the effects tend to decrease, while in cases where the amount is too large, the effects tend to reach the plateau.

<Partially Cross-Linked Methyl Polysiloxane in Present Invention>

The external preparation for skin of the present invention is an oil-gel-form external preparation for skin containing: 1) a compound represented by the General Formula (1), an isomer thereof, and/or a pharmaceutically acceptable salt thereof; and 2) a partially cross-linked methyl polysiloxane. A partially cross-linked methyl polysiloxane, which is classified as a partially cross-linked organopolysiloxane polymer, is a silicone oil having a structure in which a linear polymer formed by siloxane bonds is partially cross-linked. The term "partially cross-linked" in the present invention means a product produced by allowing cross-linking such that the crosslinking rate, which indicates the degree of cross-linking, becomes about 20 to 30%.

The partially cross-linked methyl polysiloxane used in the present invention preferably has a consistency of 100 to 500 at 25° C. from the viewpoint of stability and usability.

The consistency of the partially cross-linked methyl polysiloxane at 25° C. can be measured according to JIS K2220.

Some kinds of the partially cross-linked methyl polysiloxane are commercially available as general-purpose raw materials for cosmetics. The partially cross-linked methyl polysiloxane in the present invention may be one obtained by purchasing such a commercially available product.

The commercially available product may be one containing another silicone oil such as decamethylcyclopentasiloxane, methylpolysiloxane, octamethylcyclotetrasiloxane, or methylphenylpolysiloxane in addition to the partially cross-linked methyl polysiloxane, or may be one containing the partially cross-linked methyl polysiloxane alone.

Preferred examples of the commercially available partially cross-linked methyl polysiloxane include KSG-15 (a mixture of about 5 parts by mass of a partially cross-linked methyl polysiloxane and about 95 parts by mass of decamethylcyclopentasiloxane), KSG-16 (a mixture of about 20 to 30 parts by mass of a partially cross-linked methyl polysiloxane and about 70 to 80 parts by mass of methyl polysiloxane), KSG-17 (a mixture of about 5 parts by mass of a partially cross-linked methyl polysiloxane and about 95 parts by mass of octamethylcyclotetrasiloxane), and KSG-18 (a mixture of about 10 to 20 parts by mass of a partially cross-linked methyl polysiloxane and about 80 to 90 parts by mass of methylphenylpolysiloxane), manufactured by Shin-Etsu Chemical Co., Ltd. KSG-16 is especially preferred.

In the oil-gel-form external preparation for skin of the present invention, one or more of the commercially available products containing a partially cross-linked methyl polysiloxane may be selected and included, or another silicone oil may be included in a commercially available product containing a partially cross-linked methyl polysiloxane alone. The partially cross-linked methyl polysiloxane acts as a gel forming agent in the external preparation for skin of the present invention, and gives an action to maintain the oil gel structure of the external preparation for skin. For production of such an action, the content of the partially cross-linked methyl polysiloxane is preferably 5 to 25% by mass, more preferably 10 to 20% by mass with respect to the total amount of the oil-gel-form external preparation for skin. This is because, in cases where the content is too small, the maintenance of the structure tends to be difficult, while in cases where the content is too large, the degree of freedom of formulation tends to be deteriorated.

<External Preparation for Skin of Present Invention>

The oil-gel-form external preparation for skin of the present invention comprises: 1) a compound represented by the General Formula (1), an isomer thereof, and/or a pharmaceutically acceptable salt thereof; and 2) a partially cross-linked methyl polysiloxane. The oil-gel-form external preparation for skin of the present invention increases the concentration of the effective component in the dermis by promotion of release of the compound represented by the General Formula (1) from the preparation, improvement of the dermal retentivity, and the like, thereby effectively improving the anti-aging action and the preventive or improvement action on wrinkle formation.

In the oil-gel-form external preparation for skin of the present invention, the partially cross-linked methyl polysiloxane is used to form the oil gel formulation. In addition to the cross-linked methyl polysiloxane, a component other than the silicone oil may be further included. The silicone oil contained in the commercially available product described above functions as an oily component to be gelled in the oil gel formulation. Preferred examples of the oily component include volatile silicone oils having a boiling point of not more than 200° C. at 1 atm. Preferred examples of such volatile silicone oils include methyl polysiloxanes showing not more than 1 mPa·s at 25° C., and the above-described decamethylcyclopentasiloxane, methyl polysiloxane, and octamethylcyclotetrasiloxane.

The volatile silicone oil is preferably contained at 30 to 60% by mass with respect to the total amount of the oil-gel-form external preparation for skin. The oil-gel-form external preparation for skin of the present invention is capable of improving the dermal retentivity of the compound represented by the General Formula (1) since the oily component is gelled by the partially cross-linked methyl polysiloxane to make the preparation into the oil gel formulation. Further, due to the improvement of the dermal retentivity of the compound represented by the General Formula (1), the preventive or improvement effect on wrinkle formation can be enhanced.

The oil-gel-form external preparation for skin of the present invention preferably contains a spherical powder that enhances lipid solubility, which improves, for example, spreadability of the external preparation for skin. "Spherical" in the present invention includes not only truly spherical shapes, but also substantially spherical shapes having irregularities on the surface.

The spherical powder preferably has an average particle size of 5 to 20 μm. In cases where the average particle size is less than 5 μm, squeakiness may be strongly felt upon the application, while in cases where the average particle size is more than 20 μm, irregularities due to the spherical powder may be strongly felt.

In the present description, the particle size of the spherical powder can be measured by the Microtrac method (laser diffraction/scattering method) using, for example, the Microtrac MT3000II series, manufactured by Nikkiso Co., Ltd.

Preferred examples of the spherical powder to be included in the oil-gel-form external preparation for skin of the present invention include spherical inorganic powders such as spherical silica, spherical calcium carbonate, spherical magnesium carbonate, and spherical silicates including spherical calcium silicate and spherical magnesium silicate; and organic spherical powders such as polyamide powder, polymethyl methacrylate, and polyester powder. Among these, an organic spherical powder is more preferably used. Polymethyl methacrylate is especially preferably used.

This is because organic spherical powders have not only the usability-improving action described above, but also an action to remarkably improve the dermal retentivity of the compound represented by the General Formula (1), the isomer thereof, and/or the pharmaceutically acceptable salt thereof.

As the polymethyl methacrylate for the organic spherical powder in the present invention, a commercially available product may be used. Examples of the commercially available product include Microsphere M 330, which is commercially available from Matsumoto Yushi-Seiyaku Co., Ltd. For production of the above-described action, the spherical powder is preferably contained at 12 to 50% by mass, more preferably contained at 15 to 45% by mass, especially preferably contained at 20 to 30% by mass in terms of the total amount with respect to the total amount of the oil-gel-form external preparation for skin. This is because, in cases where the content is too small, the above effect tends to decrease, while in cases where the amount is too large, the degree of freedom of formulation is deteriorated in some cases. One or more of the spherical powders described above may be selected and included in the oil-gel-form external preparation for skin of the present invention.

The oil-gel-form external preparation for skin of the present invention may contain, in addition to these components, an arbitrary component normally used for external preparations for skin. Preferred examples of such an arbitrary component include:

oils and waxes such as macadamia nut oil, avocado oil, corn oil, olive oil, rapeseed oil, sesame oil, castor oil, safflower oil, cotton seed oil, jojoba oil, coconut oil, palm oil, liquid lanolin, hydrogenated coconut oil, hydrogenated oil, Japan wax, hydrogenated castor oil, beeswax, candelilla wax, carnauba wax, insect wax, lanolin, reduced lanolin, hard lanolin, and jojoba wax;

hydrocarbons such as liquid paraffin, squalane, pristane, ozokerite, paraffin, ceresin, vaseline, and microcrystalline wax;

higher fatty acids such as oleic acid, isostearic acid, lauric acid, myristic acid, palmitic acid, stearic acid, behenic acid, and undecylenic acid;

higher alcohols such as cetyl alcohol, stearyl alcohol, isostearyl alcohol, behenyl alcohol, octyldodecanol, myristyl alcohol, and cetostearyl alcohol;

synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethylhexanoate, neopentyl glycol dicaprate, glycerin di-2-heptylundecanoate, glycerin tri-2-ethylhexanoate, trimethylolpropane tri-2-ethylhexanoate, trimethylolpropane triisostearate, and pentaneerythritol tetra-2-ethylhexanoate;

oils such as silicone oils that are not classified into the silicones described above, for example, modified polysiloxanes including amino-modified polysiloxane, polyether-modified polysiloxane, alkyl-modified polysiloxane, and fluorine-modified polysiloxane;

anionic surfactants such as fatty acid soaps including sodium laurate and sodium palmitate, potassium lauryl sulfate, and alkyl sulfate triethanolamine ether;

cationic surfactants such as stearyltrimethylammonium chloride, benzalkonium chloride, and lauryl amine oxide;

amphoteric surfactants such as imidazoline-based amphoteric surfactants including 2-cocoyl-2-imidazolinium hydroxide-1-carboxyethyloxy disodium salt; betaine-based surfactants including alkyl betaine, amidobetaine, and sulfobetaine; and acylmethyltaurine;

nonionic surfactants such as sorbitan fatty acid esters including sorbitan monostearate and sorbitan sesquioleate; glycerin fatty acids including glyceryl monostearate; propylene glycol fatty acid esters including propylene glycol monostearate; hydrogenated castor oil derivatives; glycerin alkyl ethers; POE sorbitan fatty acid esters including POE sorbitan monooleate and polyoxyethylenesorbitan monostearate; POE sorbitol fatty acid esters including POE-sorbitol monolaurate; POE glycerin fatty acid esters including POE-glycerin monoisostearate; polyethylene glycol monooleate; POE fatty acid esters including POE distearate; POE alkyl ethers including POE 2-octyldodecyl ether; POE alkylphenyl ethers including POE nonylphenyl ether; Pluronic types; POE·POP alkyl ethers including POE·POP 2-decyltetradecyl ether; Tetronics; POE castor oil/hydrogenated castor oil derivatives including POE castor oil and POE hydrogenated castor oil; sucrose fatty acid esters; and alkyl glucosides;

polyhydric alcohols such as polyethylene glycol, glycerin, 1,3-butylene glycol, erythritol, sorbitol, xylitol, maltitol, propylene glycol, dipropylene glycol, diglycerin, isoprene glycol, 1,2-pentanediol, 2,4-hexanediol, 1,2-hexanediol, and 1,2-octanediol;

moisturizing components such as sodium pyrrolidone carboxylate, lactic acid, and sodium lactate;

powders such as sericite, mica, talc, kaolin, synthetic mica, and barium sulfate, which may be subjected to surface treatment;

inorganic pigments such as red iron oxide, yellow iron oxide, black iron oxide, cobalt oxide, ultramarine blue, iron blue, titanium oxide, and zinc oxide, which may be subjected to surface treatment;

pearl agents such as titanated mica, pearl essence, and bismuth oxychloride, which may be subjected to surface treatment;

organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Violet No. 201, and Red No. 204, which may be subjected to a laking process;

polyethylene powder, polymethyl methacrylate, and nylon powder;

para-aminobenzoic acid-based ultraviolet absorbers;
anthranilic acid-based ultraviolet absorbers;
salicylic acid-based ultraviolet absorbers;
cinnamic acid-based ultraviolet absorbers;
benzophenone-based ultraviolet absorbers;
sugar-based ultraviolet absorbers;
ultraviolet absorbers such as 2-(2'-hydroxy-5'-t-octylphenyl)benzotriazole and 4-methoxy-4'-t-butyldibenzoylmethane;

lower alcohols such as ethanol and isopropanol;
vitamin A and derivatives thereof; and vitamin Bs such as vitamin $B_6$ hydrochloride, vitamin $B_6$ tripalmitate, vitamin $B_6$ dioctanoate, vitamin $B_2$ and its derivatives, vitamin $B_{12}$, and vitamin $B_{15}$ and its derivatives;

vitamins such as vitamin Es including α-tocopherol, β-tocopherol, γ-tocopherol, and vitamin E acetate; vitamin Ds; vitamin H, pantothenic acid, pantethine, and pyrroloquinoline quinone; and antimicrobial agents such as phenoxyethanol.

The oil-gel-form external preparation for skin of the present invention can be produced by processing the essential components described above, a preferred component(s), an arbitrary component(s), and/or the like according to conventional methods. For example, it is preferably produced according to the procedure described below. The thus produced oil-gel-form external preparation for skin of the present invention may be applied to cosmetics including quasi drugs, external pharmaceutical compositions for skin, external miscellaneous goods for skin, and the like. It is especially preferably applied to cosmetics.

The compound represented by the General Formula (1), the isomer thereof, and/or the pharmaceutically acceptable salt thereof are added to an oily component such as a silicone oil, and uniformly dispersed by wet pulverization using wet pulverization means such as a ball mill or a mortar machine. By kneading of the resulting dispersion liquid with a partially cross-linked methyl polysiloxane ("KSG-16" (manufactured by Shin-Etsu Chemical Co., Ltd.)), an oil-gel-form external preparation for skin can be prepared.

Further, by adding a cyclomethicone or the like compatible therewith (for example, "DC345" (manufactured by Dow Corning Toray Co., Ltd.)), uniform dilution and control of the hardness can be achieved. In cases where the cyclomethicone is included, its content is preferably 20 to 60% by mass with respect to the total amount of the external preparation for skin.

In such cases, when the content of the partially cross-linked methyl polysiloxane is too small, the structure becomes too weak. Thus, for maintaining the stability of the formulation, the content of the partially cross-linked methyl polysiloxane is preferably adjusted to 5 to 25% by mass per 0.01 to 10% by mass of the compound represented by the General Formula (1) in the oil-gel-form external preparation for skin.

EXAMPLES

The present invention is described below in more detail by way of Examples. Needless to say, however, the present invention is not limited to these Examples.

Production Example 1: Method for Producing External Preparation for Skin for Comparison (Emulsion Formulation) in Present Invention According to the formulation shown in Table 1, an emulsion-form external preparation for skin was prepared. More specifically, Components (A) and (B) were separately heated to 70° C., and then (A) was slowly added to (B) with stirring. After cooling the resulting mixture to 40° C. with stirring, Component (C) was slowly added to the mixture, and the resulting mixture was uniformly stirred. At 30° C., the cooling and the stirring were stopped to obtain an emulsion-form external preparation for skin (Emulsion Formulation 1).

TABLE 1

| Component | Weight (g) |
|---|---|
| (A) | |
| Triglyceryl isostearate (Nikkol DIS) (manufactured by Nippon Surfactant Industries Co., Ltd.) | 10.0 |
| Cetyl alcohol (Cetanol HP) (manufactured by Kokyu Alcohol Kogyo Co., Ltd.) | 0.5 |
| Behenyl alcohol (Toho BH65) (manufactured by TOHO Chemical Industry Co., Ltd.) | 0.2 |
| Ethylparaben (manufactured by Ueno Fine Chemicals Industry, Ltd.) | 0.2 |
| Propylparaben (manufactured by Ueno Fine Chemicals Industry, Ltd.) | 0.2 |
| Glyceryl monostearate (Nikkol MGS-BV) (manufactured by Nippon Surfactant Industries Co., Ltd.) | 0.5 |
| Polyoxyethylene polyoxypropylene stearyl ether (Unisafe 34S23) (manufactured by NOF Corporation) | 1.5 |
| Polyoxyethylene (100) hydrogenated castor oil (Nikkol DC100) (manufactured by Nippon Surfactant Industries Co., Ltd.) | 0.6 |
| Dipropylene glycol (DPG-M) (manufactured by Asahi Glass Company, Limited) | 4.0 |
| (B) | |
| 1,3-Butanediol (1,3 BG) (manufactured by Daicel Chemical Industries, Ltd.) | 1.0 |

TABLE 1-continued

| Component | Weight (g) |
|---|---|
| Xanthan gum (Ketorol) (manufactured by Dainippon Pharmaceutical Co., Ltd.) | 0.3 |
| Water | 60.0 |
| (C) | |
| Compound represented by the General Formula (1) (KSK32) | 1.0 |
| Water | 20.0 |

Example 1

Production Example 2: Method for Producing Oil-Gel-Form External Preparation for Skin of Present Invention 1

After weighing 60.0 (g) of "Silicone KSG-16 (Shin-Etsu Chemical Co., Ltd.)" and 5.0 (g) of "Glyceryl Triisooctanate (Nomcort TIO) (Nisshin Oillio Group, Ltd.)", these were uniformly kneaded together. To 1.0 (g) of "KSK32", 9.0 (g) of "Glyceryl Triisooctanate" was added, and the resulting mixture was pulverized using a pulverizer to prepare a KSK32 dispersion liquid. To the dispersion liquid, 20.0 (g) of "Polymethyl Methacrylate Spherical Powder (Microsphere M 330) (Matsumoto Yushi-Seiyaku Co., Ltd.)" and 5.0 (g) of "Sericite (Sericite FSE, Sanshin Mining Ind. Co., Ltd.)" were added, and the resulting mixture was kneaded together to produce an oil gel formulation. Thus, an external preparation for skin as an oil gel formulation (Cosmetic 1) was obtained.

Comparative Production Example: Method for Producing External Preparation for Skin (Gloss Preparation) of Present Invention After weighing 10 (g) of Rheopearl KL2 (Chiba Flour Milling Co., Ltd.), 40 (g) of glyceryl triisooctanate (Nisshin Oillio Group, Ltd.), and 45 (g) of Lusplan (Nippon Fine Chemical Co., Ltd.), these were melt together by heating at 85° C. A KSK32 dispersion liquid prepared by adding 4.5 (g) of "Glyceryl Triisooctanate (Nisshin Oillio Group, Ltd.)" to 0.5 (g) of "KSK32" followed by pulverization using a pulverizer was added to the above mixture, and the temperature of the resulting mixture was allowed to cool to normal temperature with stirring and mixing, to obtain a gloss-form external preparation for skin (Comparative Example 1).

Test Example 1: Evaluation of Dermal Retentivity of Oil-Gel-Form External Preparation for Skin of Present Invention 1

The external preparation for skin for comparison (Emulsion Formulation 1), the oil-gel-form external preparation for skin (Cosmetic 1), and Comparative Example 1 (gloss preparation) produced according to the above methods were evaluated for the KSK32 dermal retentivity. In a Franz-type diffusion cell, isolated human skin (Caucasian, 50-year-old male, skin of the back) was placed, and the receptor side was filled with PBS. Each formulation prepared as described above was placed in the donor side, and then left to stand at 37° C. for 24 hours, followed by removing the residual formulation attached to the skin surface and rinsing with methanol. After removing the horny layer from the rinsed skin using a tape, KSK32 was extracted from the treated skin (the epidermal and dermal portions excluding the horny layer) using methanol, and its amount retained in the skin was calculated by HPLC (column, reverse-phase column (3.0×100 mm); column temperature, room temperature; mobile phase, aqueous anionic sulfonic acid type surfactant solution/THF 25%, pH 3; flow rate, 0.4 mL/min.; detection, 240 nm). The results are shown in Table 2. In the case where Emulsion Formulation 1 was used, KSK32 was not detected. In the gloss preparation of Comparative Example 1, a small amount of KSK32 was found to be retained. On the other hand, the oil-gel-form external preparation for skin (Cosmetic 1) showed retention of KSK32 in the skin, indicating that the dermal retentivity was improved by the oil gel formulation.

TABLE 2

| Sample | Intradermal retention at Hour 24 ($\mu g/cm^2$) |
|---|---|
| Emulsion Formulation 1 | N.D. |
| Cosmetic 1 | 1.2 |
| Comparative Example 1 (Gloss Preparation) | 0.5 |

Example 2

Production Example 3: Method for Producing Oil-Gel-Form External Preparation for Skin of Present Invention 2

After weighing 65.0 (g) of "Silicone KSG-16 (manufactured by Shin-Etsu Chemical Co., Ltd.)" and 15.0 (g) of "Nomcort TIO (Nisshin Oillio Group, Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 15.0 (g) of "Microsphere M 330 (Matsumoto Yushi-Seiyaku Co., Ltd.)" were added, and the resulting mixture was kneaded to produce an oil-gel-form external preparation for skin (Cosmetic 2).

Example 3

Production Example 4: Method for Producing Oil-Gel-Form External Preparation for Skin of Present Invention 3

After weighing 65.0 (g) of "Silicone KSG-16 (Shin-Etsu Chemical Co., Ltd.)", 15.0 (g) of "Nomcort TIO (Nisshin Oillio Group, Ltd.)", and 5.0 (g) of "Silicone KF96-6 (Shin-Etsu Silicone Co., Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 10.0 (g) of "Microsphere M 330 (Matsumoto Yushi-Seiyaku Co., Ltd.)" were added, and the resulting mixture was kneaded to produce an oil-gel-form external preparation for skin (Cosmetic 3).

Example 4

Production Example 5: Method for Producing Oil-Gel-Form External Preparation for Skin of Present Invention 4

After weighing 65.0 (g) of "Silicone KSG-16 (Shin-Etsu Chemical Co., Ltd.)", 15.0 (g) of "Nomcort TIO (Nisshin Oillio Group, Ltd.)", and 7.5 (g) of "Silicone KF96-6 (manufactured by Shin-Etsu Chemical Co., Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 7.5 (g) of "Microsphere M 330 (Matsumoto Yushi-Seiyaku Co., Ltd.)" were added, and the resulting mixture was kneaded to produce an oil-gel-form external preparation for skin (Cosmetic 4).

Example 5

Test Example 2: Evaluation of Dermal Retentivity of Oil-Gel-Form External Preparation for Skin of Present Invention 2

The microsphere formulations at different concentrations produced according to the methods described in Examples 3 to 5 (Cosmetic 2 to Cosmetic 4) were evaluated for the intradermal retentivity according to the method described in Test Example 1. The results are shown in Table 3.

TABLE 3

| Sample (amount of Microsphere M330 included (% by weight)) | Intradermal retention at Hour 24 ($\mu g/cm^2$) |
|---|---|
| Cosmetic 2 (15.0) | 0.6 |
| Cosmetic 3 (10.0) | 0.3 |
| Cosmetic 4 (7.5) | 0.2 |

It was suggested that, by increasing the content of microsphere M330 in the oil-gel-form external preparations for skin (Cosmetics 2 to 4), the dermal retentivity of KSK32 can be increased.

Example 6

Production Example 6: Method for Producing Oil-Gel-Form External Preparation for Skin of Present Invention 5

After weighing 75.0 (g) of "Silicone KSG-16 (Shin-Etsu Chemical Co., Ltd.)" and 5.0 (g) of "Nomcort TIO (Nisshin Oillio Group, Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 15.0 (g) of "Microsphere M 330 (Matsumoto Yushi-Seiyaku Co., Ltd.)" were added, and the resulting mixture was kneaded to produce an oil-gel-form external preparation for skin (Cosmetic 5).

Example 7

Production Example 7: Method for Producing Oil-Gel-Form External Preparation for Skin of Present Invention 6

After weighing 65.0 (g) of "Silicone KSG-16 (Shin-Etsu Chemical Co., Ltd.)" and 5.0 (g) of "Nomcort TIO (Nisshin Oillio Group, Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 25.0 (g) of "Microsphere M 330 (Matsumoto Yushi-Seiyaku Co., Ltd.)" were added, and the resulting mixture was kneaded to produce an oil-gel-form external preparation for skin (Cosmetic 6).

Example 8

Test Example 3: Evaluation of Dermal Retentivity of Oil-Gel-Form External Preparation for Skin of Present Invention 3

The microsphere formulations at different concentrations produced according to the methods described in Examples 6 and 7 (Cosmetic 5 and Cosmetic 6) were evaluated for the intradermal retentivity according to the method described in Test Example 1. The results are shown in Table 4.

TABLE 4

| Sample (amount of Microsphere M330 included (% by weight)) | Intradermal retention at Hour 24 ($\mu g/cm^2$) |
|---|---|
| Cosmetic 5 (15.0) | 0.5 |
| Cosmetic 6 (25.0) | 0.6 |

According to the results in Table 3 and Table 4, it was found that there is a threshold at about 15% by mass regarding the content of the spherical powder. It was found that the content of the spherical powder is preferably not less than 12% by mass, more preferably not less than 15% by mass, still more preferably not less than 20% by mass, and that the content is preferably not more than 50% by mass, more preferably not more than 45% by mass, still more preferably not more than 30% by mass.

Production Example 8: Method for Producing Oil-Gel-Form External Preparation for Skin of Present Invention 7

By kneading 71.0 (g) of "Silicone KSG-16 (Shin-Etsu Chemical Co., Ltd.)", 2.4 (g) of "Polyether-modified Silicone (Silicone KF-6017 (Shin-Etsu Chemical Co., Ltd.))", 18.3 (g) of "DC345 (Dow Corning Toray Co., Ltd.)", 0.4 (g) of "Phenoxyethanol (Yokkaichi Chemical Company, Limited)", 5.9 (g) of "Ethanol (Wako Pure Chemical Industries, Ltd.)", and 2 (g) of "KSK32" together, an oil-gel-form external preparation for skin containing no powder (external preparation for skin containing no powder) was produced.

Example 9

Production Example 9: Method for Producing Oil-Gel-Form External Preparation for Skin of Present Invention 8

"Silicone KSG-16 (manufactured by Shin-Etsu Silicone Co., Ltd.)" in an amount of 60.0 (g) and "Microsphere M 330 (Matsumoto Yushi-Seiyaku Co., Ltd.)" in an amount of 15.0 (g) were kneaded together. By kneading with 2.0 (g) of "Polyether-modified Silicone (Silicone KF-6017 (Shin-Etsu Chemical Co., Ltd.)", 15.7 (g) of "DC345 (Dow Corning Toray Co., Ltd.)", 0.3 (g) of "Phenoxyethanol (Yokkaichi Chemical Company, Limited)", 5.0 (g) of "Ethanol (Wako Pure Chemical Industries, Ltd.)", and 2.0 (g) of "KSK32", an oil-gel-form external preparation for skin containing "Polymethyl Methacrylate Spherical Powder (Microsphere M 330, Matsumoto Yushi-Seiyaku Co., Ltd.)" (Cosmetic 7) was produced.

Example 10

Production Example 10: Method for Producing Oil-Gel-Form External Preparation for Skin of Present Invention 9

"Silicone KSG-16 (Shin-Etsu Chemical Co., Ltd.)" in an amount of 60.0 (g) and "Spherical Polyamide Resin (Nylon SP 500, manufactured by Toray Industries, Inc.)" in an amount of 15.0 (g) were kneaded together. By kneading with 2.0 (g) of "Silicone KF-6017 (Shin-Etsu Chemical Co., Ltd.)", 15.7 (g) of "DC345 (Dow Corning Toray Co., Ltd.)", 0.3 (g) of "Phenoxyethanol (Yokkaichi Chemical Company, Limited)", 5.0 (g) of "Ethanol (Wako Pure Chemical Industries, Ltd.)", and 2.0 (g) of "KSK32", an oil-gel-form external preparation for skin containing a spherical polyamide resin powder (Cosmetic 8) was produced.

Example 11

Test Example 4: Evaluation of Dermal Retentivity of Oil-Gel-Form External Preparation for Skin of Present Invention 4

According to the method described in Test Example 1, the oil-gel-form external preparations for skin of the present invention (Cosmetic 7 and Cosmetic 8) were evaluated for the dermal retentivity. The results are shown in Table 5.

TABLE 5

| Sample | Intradermal retention at Hour 24 (relative to the value for the external preparation for skin containing no powder, which is taken as 1.0) |
|---|---|
| External preparation for skin of Production Example 8 | 1.0 |
| Cosmetic 7 (formulation containing microspheres) | 1.9 |
| Cosmetic 8 (formulation containing spherical polyamide resin powder) | 1.7 |

Both organic spherical powders showed higher intradermal retention compared to the preparation containing no powder. Microsphere M 330 showed an especially high dermal retentivity.

Production Example 11: Method for Producing Oil-Gel-Form External Preparation for Skin of Present Invention 10

After weighing 80.0 (g) of "Silicone KSG-16 (Shin-Etsu Chemical Co., Ltd.)" and 15.0 (g) of "Nomcort TIO (Nisshin Oillio Group, Ltd.)", these were uniformly kneaded together.

To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid was added, and the resulting mixture was kneaded to produce an oil-gel-form external preparation for skin (external preparation for skin containing no powder).

Example 12

Production Example 12: Method for Producing Oil-Gel-Form External Preparation for Skin of Present Invention 11

After weighing 65.0 (g) of "Silicone KSG-16 (Shin-Etsu Chemical Co., Ltd.)" and 15.0 (g) of "Nomcort TIO (Nisshin Oillio Group, Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 15.0 (g) of "Polymethyl Methacrylate Spherical Powder (Microsphere M 330, Matsumoto Yushi-Seiyaku Co., Ltd.)" were added, and the resulting mixture was kneaded to produce an oil-gel-form external preparation for skin (Cosmetic 9).

Example 13

Production Example 13: Method for Producing Oil-Gel-Form External Preparation for Skin of Present Invention 12

After weighing 65.0 (g) of "Silicone KSG-16 (Shin-Etsu Chemical Co., Ltd.)" and 15.0 (g) of "Nomcort TIO (Nisshin Oillio Group, Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 15.0 (g) of "Sericite (Sericite FSE, Sanshin Mining Ind. Co., Ltd.)" were added, and the resulting mixture was kneaded to produce an oil-gel-form external preparation for skin (Cosmetic 10).

Example 14

Test Example 5: Evaluation of Dermal Retentivity of Oil-Gel-Form External Preparation for Skin of Present Invention 5

The oil-gel-form external preparations for skin of the present invention produced according to the methods described in Production Example 11, Example 11, and Example 12 (the external preparation for skin containing no powder, and Cosmetics 9 and 10) were evaluated for the dermal retentivity according to the method described in Test Example 1. The results are shown in Table 6.

The intradermal retentivities of the formulation containing no powder, the formulation containing microspheres, and the formulation containing sericite (silicate mineral) were tested according to the method described above, and compared.

TABLE 6

| Sample | Intradermal retention at Hour 24 (relative to the value for the preparation containing no powder) |
|---|---|
| Cosmetic 9 (formulation containing microspheres) | 2.2 |
| Cosmetic 10 (formulation containing Sericite powder) | 1.0 |

Cosmetic 9, which is a formulation containing microspheres as a spherical powder, showed a higher level of intradermal retention compared to Cosmetic 10, which is a formulation containing the plate-like powder "Sericite".

Example 15

Production Example 14: Method for Producing Oil-Gel-Form External Preparation for Skin of Present Invention 13

After weighing 65.0 (g) of "Silicone KSG-16 (Shin-Etsu Chemical Co., Ltd.)" and 15.0 (g) of "Nomcort TIO (Nisshin Oillio Group, Ltd.)", these were uniformly kneaded together. To 0.5 (g) of "KSK32", 4.5 (g) of "DC345 (Dow Corning Toray Co., Ltd.)" was added, and the resulting mixture was pulverized using a pulverizer to prepare a KSK32 dispersion liquid. To the composition of KSG-16 and Nomcort TIO, the KSK32 dispersion liquid and 15.0 (g) of spherical silicic anhydride "Silica Microbead P 1500 (Catalysts & Chemicals Industries Co., Ltd.)" were added, and the resulting mixture was kneaded to produce an oil-gel-form external preparation for skin (Cosmetic 11).

Example 16

Test Example 5: Evaluation of Dermal Retentivity of Oil-Gel-Form External Preparation for Skin of Present Invention 5

Cosmetic 9, and the oil-gel-form external preparation for skin of the present invention produced according to Example 15 (Cosmetic 11) were evaluated for the dermal retentivity according to the method described in Test Example 1. The results are shown in Table 7.

TABLE 7

| Sample | Intradermal retention at Hour 24 (relative to the value for the preparation containing no powder) |
|---|---|
| Cosmetic 9 (formulation containing microspheres) | 2.2 |
| Cosmetic 11 (formulation containing silica microbeads) | 0.9 |

The oil-gel-form external preparation for skin containing silica microbeads (Cosmetic 11) as a representative example of spherical inorganic powders was evaluated for the dermal retentivity. As a result, the preparation showed a lower dermal retentivity compared to the organic spherical powder.

INDUSTRIAL APPLICABILITY

The present invention is practically applicable to external preparations for skin such as cosmetics.

What is claimed is:

1. An oil-gel-form external preparation for skin, comprising:
   1) a compound represented by the following General Formula (1):

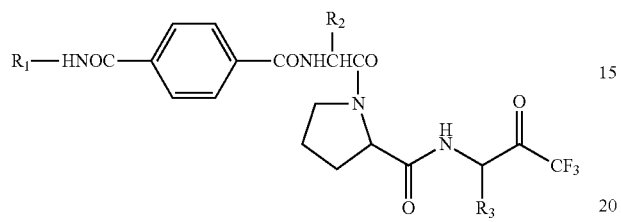

wherein in the formula, $R_1$ represents a $C_1$-$C_4$ linear or branched alkyl group substituted by a carboxyl group(s), or a $C_1$-$C_4$ linear or branched alkyl group substituted by a carboxylic acid ester group(s) having a $C_1$-$C_4$ alkyl chain; and $R_2$ and $R_3$ each independently represent a $C_1$-$C_4$ linear or branched alkyl group, an isomer thereof, and/or a pharmaceutically acceptable salt thereof; and 2) a partially cross-linked methyl polysiloxane.

2. The oil-gel-form external preparation for skin according to claim 1, wherein the compound represented by the General Formula (1) is a compound represented by the following General Formula (2):

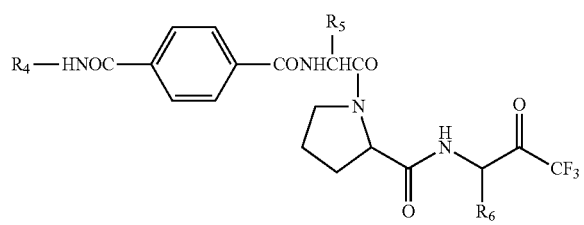

wherein in the formula, $R_4$ represents a $C_1$-$C_4$ linear or branched alkyl group substituted by a carboxyl group(s); and $R_5$ and $R_6$ each independently represent a $C_1$-$C_4$ linear or branched alkyl group, an isomer thereof, and/or a pharmaceutically acceptable salt thereof.

3. The oil-gel-form external preparation for skin according to claim 2, wherein the compound represented by the General Formula (2) is 3(RS)-[[4-(carboxymethylaminocarbonyl)phenylcarbonyl]-L-valyl-L-prolyl]amino-1,1,1-trifluoro-4-methyl-2-oxopentane represented by the following Formula (3):

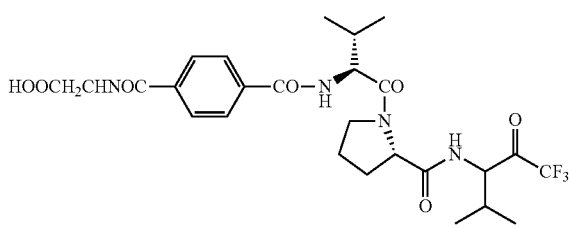

an isomer thereof, and/or a pharmaceutically acceptable salt thereof.

4. The oil-gel-form external preparation for skin according to claim 1, further comprising a spherical powder.

5. The oil-gel-form external preparation for skin according to claim 4, wherein the spherical powder is an organic spherical powder.

6. The oil-gel-form external preparation for skin according to claim 4, wherein the spherical powder is polymethyl methacrylate.

7. The oil-gel-form external preparation for skin according to claim 4, wherein the spherical powder is contained at 12 to 50% by mass with respect to the total amount of the external preparation for skin.

* * * * *

UNITED STATES PATENT AND TRADEMARK OFFICE
CERTIFICATE OF CORRECTION

PATENT NO. : 11,413,224 B2
APPLICATION NO. : 16/306881
DATED : August 16, 2022
INVENTOR(S) : Toshihiro Hinokitani et al.

It is certified that error appears in the above-identified patent and that said Letters Patent is hereby corrected as shown below:

On the Title Page

Column 2 (Other Publications), Line 1, delete "translattion." and insert -- translation. --.

Column 2 (Other Publications), Line 2-3, delete "translattion." and insert -- translation. --.

Column 2 (Other Publications), Line 4, delete "translattion." and insert -- translation. --.

In the Specification

Column 11, Line 34, delete "pentaneerythritol" and insert -- pentaerythritol --.

Signed and Sealed this
Twenty-first Day of February, 2023

Katherine Kelly Vidal
*Director of the United States Patent and Trademark Office*